United States Patent

Cole et al.

[11] Patent Number: 6,039,746
[45] Date of Patent: Mar. 21, 2000

[54] PATCH ELECTROLYSIS SYSTEM AND METHOD FOR REMOVING HAIR FROM SKIN

[76] Inventors: Hubert L. Cole, 160 S. May St., Southern Pines, N.C. 28387; Mark H. Chandler, 830 Monticello Dr., Pinehurst, N.C. 28374

[21] Appl. No.: 09/280,926

[22] Filed: Mar. 29, 1999

[51] Int. Cl.[7] ................................................. A61B 17/50
[52] U.S. Cl. ............................................................. 606/133
[58] Field of Search .............................. 606/36, 43, 131, 606/133

[56] References Cited

U.S. PATENT DOCUMENTS

| | | | |
|---|---|---|---|
| 4,777,954 | 10/1988 | Keusch et al. | 128/640 |
| 5,522,814 | 6/1996 | Bernaz | 606/43 |
| 5,797,926 | 8/1998 | Mehl, Sr. | 606/43 |
| 5,824,033 | 10/1998 | Ferrari | 607/142 |
| 5,846,252 | 12/1998 | Mehl, Sr. | 606/36 |

FOREIGN PATENT DOCUMENTS

96/03928  2/1996  WIPO ..................................... 606/36

*Primary Examiner*—Jeffrey A. Smith
*Assistant Examiner*—Eduardo C. Robert
*Attorney, Agent, or Firm*—Coats & Bennett, P.L.L.C.

[57] ABSTRACT

An electrolysis system comprises one or more patches that are secured to a skin surface. Electric current generated by an electrolysis machine directs electric current between the one or more patches and the underlying skin area. This electric current is effective to be transmitted along hair follicles underlying the patches so as to perform an electrolysis operation on the underlying hair. After a selected time period of decomposition, the hairs underlying the patch can be easily removed from the patient's skin.

13 Claims, 2 Drawing Sheets

PATCH ELECTROLYSIS SYSTEM AND METHOD FOR REMOVING HAIR FROM SKIN

FIELD OF THE INVENTION

The present invention relates to electrolysis and more particularly to removing a group of hairs from a selected area of skin through a single electrolysis operation.

BACKGROUND OF THE INVENTION

Electrolysis has long been used for removing hair from the face and other areas of the body. In typical electrolysis processes, subjects of the treatment have been able to selectively target hairs and remove them.

To understand electrolysis, it is beneficial to appreciate that at the base of each hair follicle there is a solution of salt water that is capable of conducing electricity. In particular, subjecting the salt water solution to an electric current causes the salt (NaCl) and the water ($H_2O$) to break down into their constituent chemical parts. The breakdown of the salt and water is referred to as electrolysis, and the subsequent rearrangement of the salt and water is referred to as ionization. Effectively the electrolysis, through ionization, forms sodium hydroxide (NaOH). The sodium hydroxide produced is highly caustic to the hair follicle and causes the follicle to die through a decomposition process. The general epithelium of the follicle is killed, rendering the follicle unable to ever produce more hair. Once the hair follicle passes through the decomposition process, the hair associated with the hair follicle can be extracted or in some cases the hair may even simply fall out.

As pointed out above, the electrolysis process is not new and there have been a number of basic approaches to removing hair from the facial areas and other body areas of a person. For many years the primary approach to electrolysis entailed an electrified needle that was injected into a particular hair follicle. While this electrolysis process was once widely used, it nevertheless has many drawbacks and shortcomings. First of all, it was an invasive process and with that comes pain, apprehension and anxiety by those people being treated. Further it entails a process that requires treating one hair at a time and as such it is a tedious, time consuming process.

In the patent to Cole, U.S. Pat. No. 5,026,369, a tweezer type electrolysis process was disclosed. Here a tweezer is connected or otherwise engaged with one or more hairs at a time. Current is conducted through the tweezer and by conducting current along the hair the salt and water surrounding the hair follicle is transformed to sodium hydroxide and consequently decomposition of the hair follicle occurs. Again, this process has been used substantially and has met with success. But again, this process still deals with treating one or a few hairs at a time and because of that it is a time consuming and tedious process.

Next, Cole in U.S. Pat. No. 5,534,003 introduced another procedure for performing electrolysis on hairs within a generally localized area. This patent teaches the use of an electrified probe that engages a very small area of the subject's skin and electric current is directed to the hairs occupying the very small localized area being treated. Like the prior discussed electrolysis process, current is directed down to the hair follicles and reaches the base where it transforms the salt and water to sodium chloride, giving rise to decomposition. This process and approach to electrolysis has met with substantial success because it is non-invasive and more efficient than the tweezer process disclosed in U.S. Pat. No. 5,026,369. However, the electrified probe process still requires the full attention of the electrolysis practitioner during the entire process. That is, it requires the constant attention and work of the electrolysis professional because the probe itself must be handled and moved across the localized area during the course of the process.

Therefore, there has been and continues to be a need for an electrolysis system and process that is relatively easy to administer and which preferably can be achieved without a practitioner having to constantly maintain a tweezer or an electrified probe in contact the selected hairs to be removed.

SUMMARY OF THE INVENTION

The present invention entails an electrolysis system or apparatus along with an electrolysis process, that is aimed at overcoming the problems and short comings of prior art electrolysis processes. Accordingly, the present invention entails an electrolysis process that utilizes one or more patches or surface electrodes that are selectively positioned on the skin and which are effective to conduct electricity between the underlying skin and the patch itself. That is, current is generally uniformly transmitted through the patch and in the process the underlying hair is subject to a DC current and thus substantially all or a substantial number of hairs underlying the patch are subjected to electrolysis in one single operation. After the electrolysis treatment, the one or more patches are removed from the subject's skin and after a selected period of time the individual hairs are extracted or otherwise fall from the skin.

In addition, the present process entails transmitting current between the skin and the patch for a time period of approximately 5 to 20 minutes. It has been discovered that by subjecting the hair follicles to this extended treatment results in the area in and around the hair follicles swelling which is a natural reaction of the body to the electrolysis process. This in turn results in the body supplying more salt water to the area in and around the base of the hair follicle. As additional salt water is supplied, it follows that this increases the conductivity of the hair follicle, and since there is additional salt water available, additional sodium hydroxide is produced. In the end, this significantly increases the efficiency of the electrolysis process.

It is therefore an object of the present invention to provide a hands-free electrolysis process.

Another object of the present invention is to provide an efficient electrolysis process.

Other objects and advantages of the present invention will become apparent and obvious from a study of the following description and the accompanying drawings which are merely illustrative of such invention.

DESCRIPTION OF THE INVENTION

Figure 1:
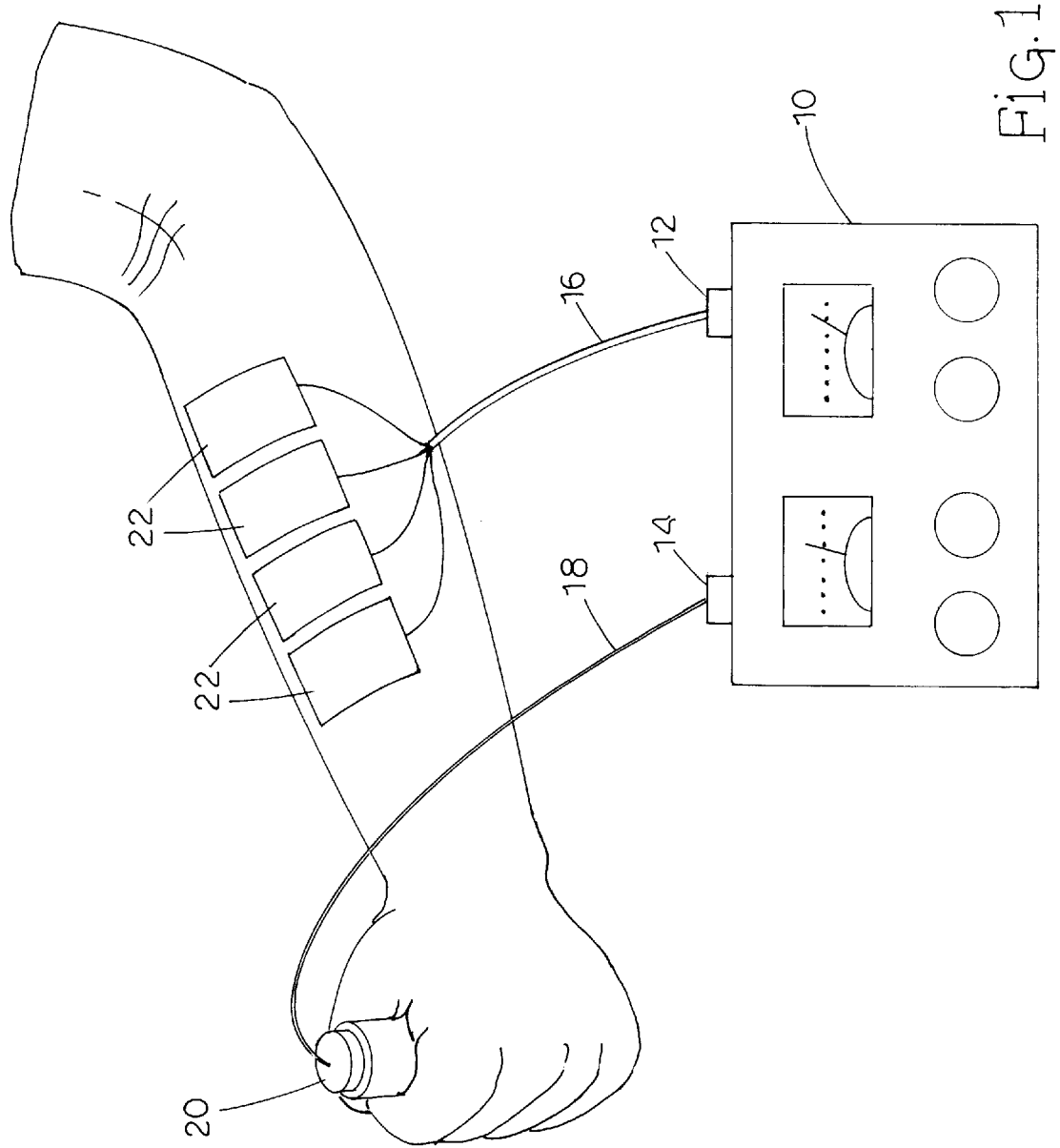
FIG. 1 illustrates the electrolysis system of the present invention and the process of conducting an electrolysis operation through one or more conductive patches that secure directly to the skin of the patient.

With further reference to the drawings, the electrolysis system of the present invention is shown therein. Before discussing the process, it may be beneficial to describe the basic components of the electrolysis system. First the electrolysis system comprises a electrolysis machine 10. Electrolysis machine 10 is of the general type that is manufactured and sold by International Hair Removal of Southern Pines, North Carolina. The electrolysis machine 10 includes two terminals 12 and 14. Connected to terminal 12 is a set of leads 16 that split and connect to a series of current conducting patches or surface electrodes 22. Connected to the other terminal 14 is a lead 18 that extends to a ground terminal 20 that is typically held or touched by the patient. For a more complete understanding of basic electrolysis processes of the prior art and the systems used, one is referred to the disclosure found in U.S. Pat. No. 5,026,639 and U.S. Pat. No. 5,534,003, both being invented by H. Lee Cole. The disclosures of these two patents are expressly incorporated herein by reference.

In the present process, current is directed between the respective patches 22 and the underlying skin of the patient. Consequently, the patches 22 are of the type suitable for conducting electricity, particularly a DC current. Their design is such that current is generally uniformly distributed over substantially the entire area of the patch 22. This assures electrical contact with all or substantially all of the hair underlying the respective patch.

In one embodiment, the patch 22 would include its own gel film or layer disposed about the underside of the patch. That is the gel that assists in conducting current between the patch 22 and the skin and underlying hairs could be impregnated into the lower surface of the patch or otherwise formed within the patch. In another embodiment, the gel could be applied to the skin surface of the patient or to the patch before the patch 22 is actually applied.

The present process entails a continuous electrolysis process that would typically last between 5 and 20 minutes. The duration of the process will depend on a number of factors, including the conductivity of the patient's skin, the type of hair being treated, and other factors that are commonly considered in performing electrolysis.

In an electrolysis process, the electrolysis machine 10 produces a DC current between approximately 500 and 2500 micro amps. The current will vary depending on the number of patches employed. For a typical electrolysis machine, it is envisioned that for patches having an area of approximately 2–5 square inches, that 1 to 6 patches could be utilized. In the case of a single patch, the DC current directed between the patch and the patient would be approximately 500 to 1000 micro amps. In the case of six patches, the current load between the patches and the skin would be approximately 1000–2500 micro amps. These current ranges can again very depending on the size and capacity of the electrolysis machine 10 and other conditions relating to the conductivity of the skin and the type of hair being removed through electrolysis.

It has been discovered that by utilizing a continuous process over a period of 5 to 20 minutes, that the efficiency of the electrolysis process is improved. This is because the natural functions of the body, in response to an electrolysis process, naturally works to increase the conductivity of the hair follicles. It is postulated that because the stress placed on the hair follicles in the first place by the electrolysis process, that the area in and around the base of the hair follicle will swell and in the process will result in the body producing additional salt water that will move into the hair follicle area. By directing additional salt water to the site, this increases conductivity in this area and produces more sodium hydroxide which results in a more caustic effect on the hair follicle.

Figure 2:
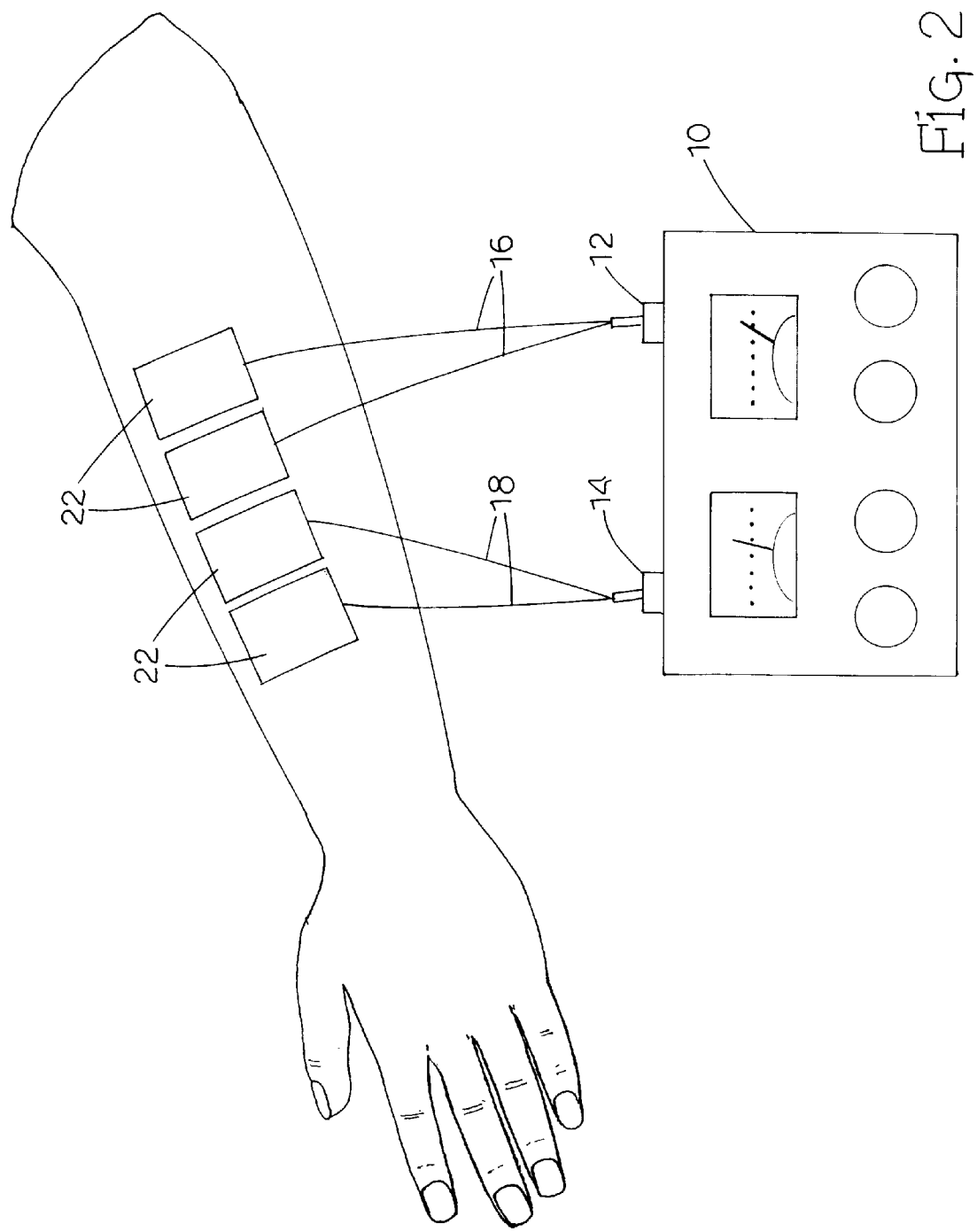
FIG. 2 also shows the electrolysis system and procedure of the present invention, but indicates an alternate way of completing the circuit between the patient and the electrolysis machine.

In FIG. 1, the process is carried out by utilizing a ground terminal 20 that effectively completes the circuit between the subject's body and the terminals of the electrolysis machine. However, it is appreciated that in cases where more than one patch 22 is used, that the patches can be divided and connected directly to both terminals 21 and 14. This is illustrated in FIG. 2. Thus in both approaches, there is a completed circuit between the patient's body and the terminals 12 and 14 of the electrolysis machine.

From the foregoing specification, it is appreciated that the electrolysis process of the present invention provides for "hands free" treatment. Once a patch or group of patches have been attached the skin of the patient, then the operator or person overseeing the electrolysis process is not required to work with a tweezer or even an electrified probe. The patches themselves, while being secured to the skin surface, act to transmit electric current between the skin and the patches themselves. Thus the electrolysis process of the present invention is non-invasive, painless, easy to administer, and has the advantage of performing electrolysis on a relatively large number of hairs underlying the patches.

I claim:

1. A method of performing electrolysis treatment on a patient via a patch, comprising:
   a. securing a patch to a person's skin and providing a gel interface between the patch and the person's skin; and
   b. directing a DC current through the patch and in the process directing the DC current to multi-hair follicles underlying the patch so as to perform an electrolysis treatment on certain hair follicles underlying the patch.

2. The method of claim 1 wherein the gel interface is applied to the skin prior to the patch being secured to the skin.

3. The method of claim 1 wherein the gel interface comprises a gel film that forms a part of the patch.

4. The method of claim 1 wherein a series of patches are connected to an electrolysis machine and applied to different areas of the patient's skin so as to perform an electrolysis treatment on certain hair follicles found in the distinct areas covered by the series of patches.

5. The method of claim 1 wherein the patch is connected to an electrolysis machine such that current moves both through the patch and the patient receiving the electrolysis treatment.

6. The method of claim 1 wherein at least two patches are secured to the patient's skin and to an electrolysis machine such that current flows through the patient and between the patches and effectively completes a circuit with respect to the electrolysis machine.

7. The method of claim 1 wherein a current is directed between the patch and the hair follicles for approximately 5 to 20 minutes.

8. The method of claim 7 wherein the current being directed between the patch and the hair follicles is approximately 500–2500 microamps.

9. The method of claim 1 wherein at least six patches are secured to the patient's skin so as to cover six distinct areas, and wherein the patches are connected to an electrolysis machine that directs a DC current between each patch and certain hair follicles underlying the patch.

10. The method of claim 9 wherein the electrolysis treatment extends for a period for approximately 5–20 minutes.

11. The method of claim 1 including conducting the electrolysis treatment for approximately 5–20 minutes.

12. The method of claim 11 including conducting the electrolysis treatment for a time period sufficient to permit the person's body to direct additional salt water to the vicinity of the hair follicles being treated so as to increase the conductivity of the hair follicles which in turn improves the efficiency of the electrolysis process.

13. The electrolysis method of claim 1 including dispersing the DC current throughout substantially the area of the patch such that current is generally transmitted between the patch as a whole and the hairs underlying the patch, thereby resulting in electrolysis being performed on a plurality of the hair underlying the patch.

* * * * *